United States Patent [19]

Brookes

[11] Patent Number: 4,710,634

[45] Date of Patent: Dec. 1, 1987

[54] SANITARY DOOR HANDLE HAVING AN UPPER HOUSING AND A SPACER ELEMENT

[76] Inventor: Richard L. Brookes, 2894 General Motors Blvd., Detroit, Mich. 48202

[21] Appl. No.: 851,956

[22] Filed: Apr. 14, 1986

[51] Int. Cl.⁴ ............................................. G01N 21/00
[52] U.S. Cl. .............................. 250/455.1; 16/110 R; 250/504 R
[58] Field of Search ............. 16/110 R; 179/184, 185; 422/24; 250/454.1, 492.1, 504 R, 504 H, 455.1; 379/433, 439, 447, 452

[56] References Cited

U.S. PATENT DOCUMENTS

| | | | |
|---|---|---|---|
| 2,339,085 | 1/1944 | Luckiesh | 250/454.1 X |
| 2,738,428 | 3/1956 | Dressel, Jr. et al. | 422/24 X |
| 2,763,735 | 9/1956 | Wahl . | |
| 3,272,927 | 9/1966 | Peebles | 179/185 |
| 3,314,746 | 4/1967 | Millar | 250/504 X |
| 3,877,152 | 4/1975 | Gorman | 422/24 X |
| 3,906,236 | 9/1975 | Callahan | 422/24 X |
| 3,955,922 | 5/1976 | Moulthrop . | |

*Primary Examiner*—Fred Silverberg
*Attorney, Agent, or Firm*—Brooks & Kushman

[57] ABSTRACT

A self-sanitizing door handle for restrooms is disclosed. The door handle has a plate having a pushing surface facing away from the door and mounted upon a hollow spacer element upon the door. A peripheral flange upon the spacer element is spaced from the door proving gripping surfaces. A housing enclosing an ultraviolet light source overlies the spacer element and directs germicidal light rays over the pushing and gripping surfaces.

10 Claims, 5 Drawing Figures

SANITARY DOOR HANDLE HAVING AN UPPER HOUSING AND A SPACER ELEMENT

RELATED APPLICATION

This application is related to copending patent application Ser. No. 734,870 filed May 16, 1985, now abandoned.

BACKGROUND OF THE INVENTION

1. Technical Field

This invention relates to an improved door handle which automatically sanitizes itself by means of germicidal light rays.

Particularly, this invention relates to door handles used in public restrooms or other public buildings.

2. Description Of Background Art

Door handles for public restrooms and other public places are repeatedly contacted by persons entering and exiting such places. While many patrons are careful about personal hygiene, some inevitably use less than adequate care to wash their hands. Since both careful and careless persons must contact the handle of the door upon leaving the restroom, germs deposited by careless users of such facilities may be transmitted to subsequent users.

Periodic cleaning of the door handle falls short of achieving the desired level of sanitation because it is not feasible to clean restroom door handles after each use with traditional cleaning methods.

The use of ultra-violet light to sanitize objects is known as is evidenced by U.S. Pat. No. 3,955,922 to Moulthrop which discloses a sterilizer for bathroom articles such as toothbrushes, dentures, combs and hairbrushes. Similarly, U.S. Pat. No. 2,738,428 to Dressel, Jr., et al. relates to an ultraviolet light sterilizing apparatus for drinking glasses. U.S. Pat. No. 2,763,735 to Wahl discloses a sterilizing attachment for telephones which makes use of an ultra-violet light bulb to kill bacteria deposited on public telephones. Even though the use of ultra-violet light for sanitizing objects is known and the problem of maintaining an acceptable level of sanitation on surfaces of restroom door handles is a long standing problem, none of the prior art patents have addressed the problem solved by this invention or suggested the unique solution disclosed herein.

It is a primary object of the invention to provide a continuously operated sanitized apparatus for portions of door handles contacted by human hands.

Another object is to provide a handle structure for use as either a push-plate or a pull handle which is sanitized by ultra-violet light impinging upon the surfaces of the handle touched by hands.

The continuously operated, self-sterilizing door handle of the present invention is a simple and unique apparatus for maintaining pushing and gripping surfaces in a sanitary condition.

SUMMARY OF THE INVENTION

A sanitary door handle is provided wherein a housing encloses a source of germicidal light rays, such an one or more ultra-violet light bulbs which directs germicidal light rays to impinge upon the outer pushing and gripping surfaces of the handle. The door handle and housing includes an electrical circuit for continuously energizing the source of germicidal light rays and for illuminating the handle.

An important feature is to provide a light housing which overlies a spacer element and push plate thereon and includes an elongated reflector enclosing the light source for impinging germicidal rays upon the push plate and upon the gripping surfaces of the spacer element in a continuous manner.

As another feature, the light housing overlies and extends transversely of the spacer element which mounts the push plate and the gripping surfaces, wherein there is provided an apertured reticulated bottom wall for directing germicidal light rays from the light source or sources downwardly onto the pushing surfaces and gripping surfaces in a continuous manner.

As another feature push plate is of a translucent material and there is provided upon the interior of the spacer element a light source for illuminating the push plate which is continuously energized in an electrical circuit along with the ultra-violet light bulbs in a continuous manner.

These and other objects and features will be seen from the following specification and claims in conjunction with the appended drawings.

It will be understood that the above drawings illustrate merely a preferred embodiment of the invention, and that other embodiments are contemplated within the scope of the claims hereafter set forth.

DETAILED DESCRIPTION

Figure 1:
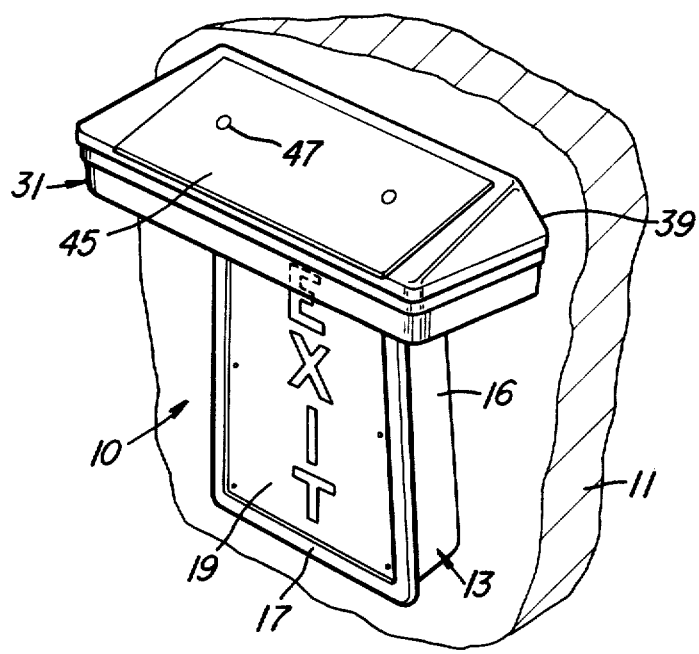
FIG. 1 is a front perspective view of the present, sanitary door handle mounted upon a door, fragmentarily shown.
Figure 2:
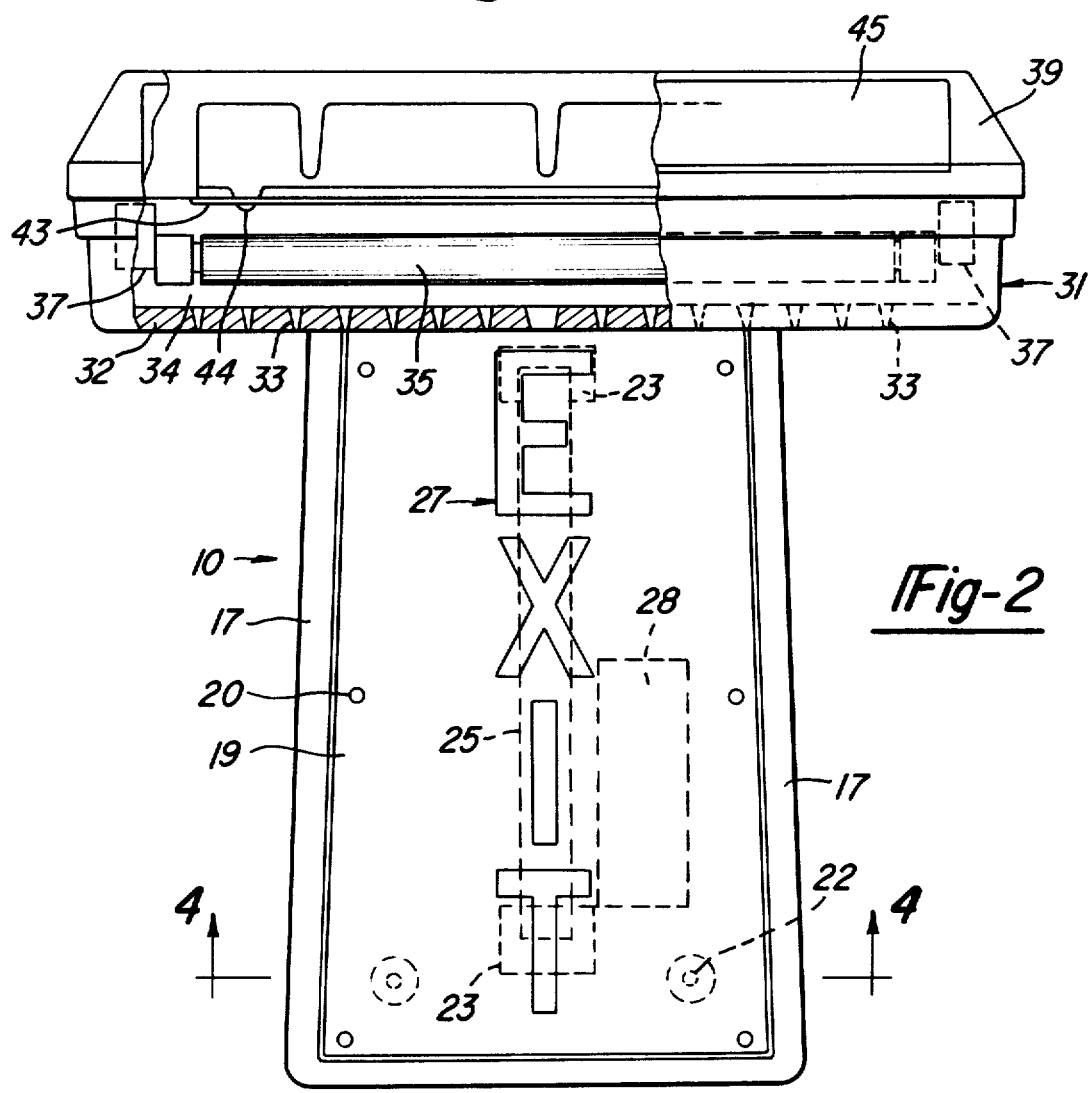
FIG. 2 is a fragmentary partly broken away and sectioned front elevational view of the door handle shown in FIG. 1, on an increased scale.
Figure 3:
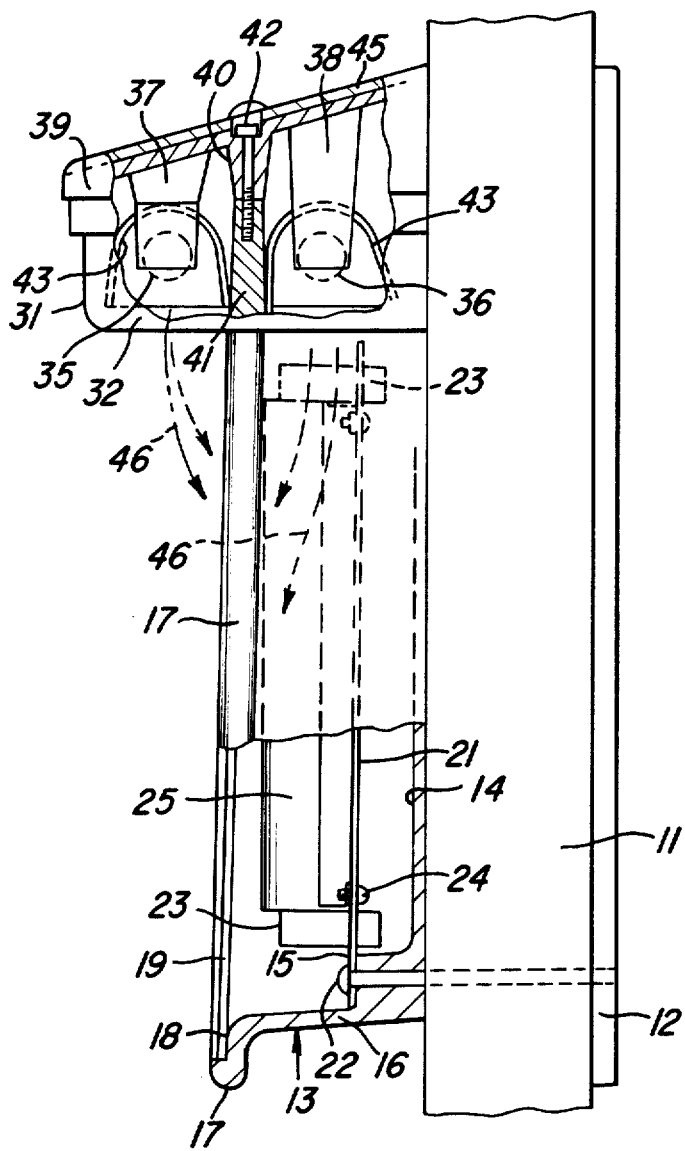
FIG. 3 is a side elevational view thereof with portions partly broken away and in section.

Referring to the drawings, FIGS. 1 through 4, the present sanitary door handle 10 is mounted upon door 11, fragmentarily shown in FIGS. 1 and 3, and in the preferred embodiment employing anchor plate 12.

Upright spacer element 13 includes a base 14 which bears against said door and includes inset apertured shoulders 15 and peripheral edges 16 upon the sides and bottom. Said sides and bottom terminate in a peripheral outturned flange 17 which is arranged outwardly of the rectangular inset edge 18 within which is nested push plate 19 retained in position by suitable fasteners 20, FIG. 2.

In the illustrative embodiment, the push plate is constructed of glass or a plastic material normally translucent and colored blue. Upright insulating mount plate 21 is positioned within spacer element 13 and bears against shoulders 15. A plurality of fasteners 22 extend through mount plate 21, through the spacer element, through corresponding openings in door 11 and in the illustrative embodiment extend into and connect anchor plate 12. It is contemplated that the anchor plate may be omitted and the fasteners 22 retainingly extend into said door.

Supported upon mount plate 21 are a pair of opposing spaced electrical receptacles 23 suitably secured thereto in an insulated relation as at 24 and a well-known manner adapted to receive and support light bulb 25. In the illustrative embodiment bulb 25 is a fluorescent lighting tube delivering white light when energized for illuminating plate 19 which has an exterior pushing surface facing away from said door.

Figure 5:
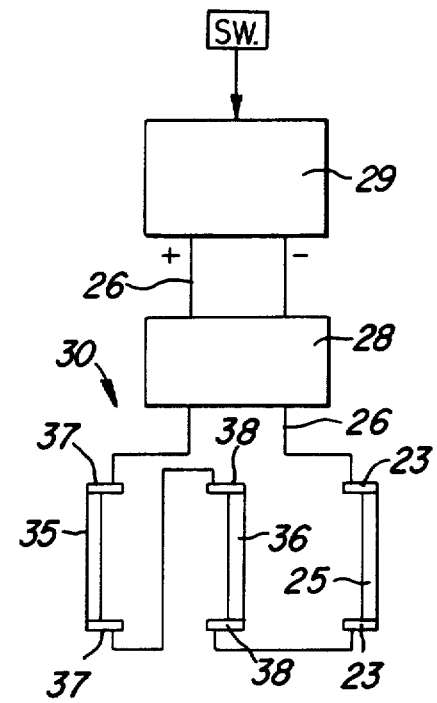
FIG. 5 is a schematic wiring diagram.
Figure 4:
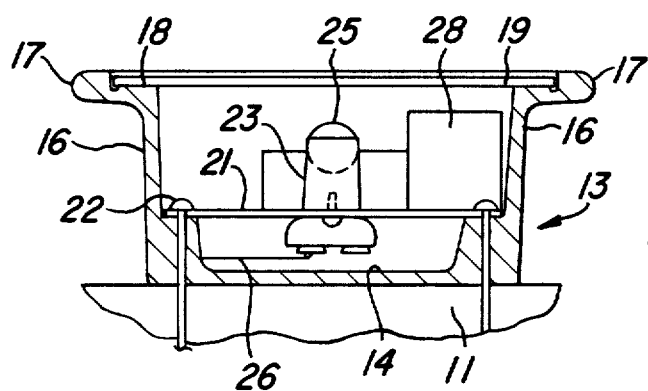
FIG. 4 is a fragmentary section taken in the direction of arrows 4—4 of FIG. 2.

A suitable electrical circuit 30 is shown in FIG. 5 which includes leads 26 to receptacles 23, to the inverter 28, sometimes referred to as ballast in the event that bulb 25 is a fluorescent lighting tube. The circuit includes an electrical power source 29, 110 Volts for illustration, and a connected off and on switch designated SW, which may be a conventional light switch.

Elongated light housing 31 is arranged above and extends transversely over spacer element 13 and bears against door 11, FIG. 3. The light housing includes bottom wall 32 which is reticulated. Wall 32 includes a series of laterally spaced rows of longitudinally spaced converging apertures 33, FIG. 2, for directing germicidal light rays 46 down onto the pushing surface of push plate 19 and the gripping surfaces 17 corresponding to the peripheral flange 17 on spacer element 13.

Housing 31 includes light chamber 34 which may hold one or in the preferred embodiment a pair of first and second ultra-violet light bulbs or tubes 35 and 36 supported between opposed pairs of electric receptacles 37 and 38 in the electrical circuit, FIG. 5. As illustrated in FIG. 3, housing 31 includes removably positioned thereover slant top cover 39 having a pair of depending apertured mount bosses 40 in registry with a similar boss or divider 41 within housing 41 adapted to receive fasteners 42.

Mounted within housing 31 supportively depending from cover 39 corresponding to the pair of ultra-violet light tubes 35 and 36 are a pair of downwardly opening elongated U-shaped reflectors 43. These are secured at 44 to corresponding portions of the cover, FIG. 2.

Accordingly, the respective reflectors 43, sometimes referred to as means disposed in the housing for directing the rays of ultra-violet light so as to impinge upon pushing surface 19 of the push plate and the gripping surfaces 17 on the perimeter of spacer element 13. The reflectors direct the germicidal ultra-violet light rays 46, FIG. 2, so as to respectively impinge upon push surfaces 19 and gripping surfaces 17 sanitizing said handle surfaces.

In the illustrative embodiment, upon slant top cover 39 there is provided a rectangular recess within which is positioned the inset cover plate 45 normally closing off access to fasteners 42. In the illustrative embodiment a pair of longitudinally spaced apertures 47 are formed in cover plate 45 to permit screw driver access to fasteners 42, if desired.

The light bulb 25, preferably a white light fluorescent tube, FIGS. 2 and 3, illuminate the interior of spacer element 13 and particularly the indicia 27, which in the illustrative embodiment is an exit sign directly applied to push plate 19.

In view of the illustrative circuit 30, FIG. 5, the lead wires 26 from power source 29 and switch SW, including inverter 28, are connected in a series circuit arrangement to the respective fluorescent tubes 25, 35 and 36 for continuous illumination thereof.

There has been provided, in accordance with the invention, a self-sanitizing door handle that fully satisfies the object, aims, and advantages set forth above. While the invention has been described in conjunction with a specific embodiment thereof, it is evident that many alternatives, modifications, and variations will be apparent to those skilled in the art in view of the foregoing description. Accordingly, it is intended to embrace all alternatives, modifications and variations that fall within the spirit and scope of the following claims.

I claim:
1. A sanitary door handle comprising:
   a plate having a pushing surface facing away from the door;
   a spacer element mounting and interconnecting the plate and door;
   a peripheral flange upon the spacer extending outwardly from the plate;
   said flange having a gripping surface spaced from and facing the door;
   a housing being located above the plate;
   said housing including a removable cover and also including a light chamber within the housing;
   said light chamber including an ultraviolet germicidal light source;
   said cover including a downwardly and forwardly slanted top having a cut away rectangular recess therein, a corresponding shaped access plate being nested within the cover recess; and
   shielding means supported on and depending from the cover and enclosing the light source for directing the ultraviolet germicidal light upon the pushing and gripping surfaces to thereby sanitize the handle and shield points above the housing from exposure to the ultraviolet light.

2. The self sanitizing door handle of claim 1, wherein said housing is mounted upon and extends transversely of said spacer element.

3. The self sanitizing door handle of claim 1 wherein the source of said light is a pair of laterally spaced ultraviolet light bulbs within the chamber.

4. The self sanitizing door handle of claim 3, wherein said shielding means includes a pair of laterally spaced elongated downturned reflectors of general U-shape supported within the housing and enclosing the bulbs respectively.

5. The self sanitizing door handle of claim 1, wherein said housing includes a bottom wall upon the housing having formed therein a series of reticulated converging apertures therethrough for directing ultraviolet light rays to the surfaces.

6. The self sanitizing door handle of claim 5, wherein said apertures are longitudinally spaced and in laterally spaced rows.

7. The self sanitizing door handle of claim 5, wherein said cover has opposed pairs of electrical receptacles depending therefrom;
   said bulbs at their ends being supported within the pairs of receptacles whereby removal of the cover facilitates access to said bulbs.

8. The self sanitizing door handle of claim 5, wherein the plate is translucent,
   a pair of opposed spaced electrical receptacles being within the spacer element,
   a fluorescent light bulb being mounted within the receptacles for illuminating the push plate, and
   an electrical circuit including a power source and an inverter being connected to all of the bulbs for simultaneous and continuous energization thereof.

9. The self sanitizing door handle of claim 1, wherein said shielding means includes an elongated down-turned reflector of general U-shape supported within the housing and enclosing the bulb.

10. The self sanitizing door handle of claim 1, wherein said plate is translucent,
    a pair of opposed spaced electrical receptacles being within the spacer element, and
    a fluorescent light bulb being mounted within the receptacles for illuminating the push plate.

* * * * *

UNITED STATES PATENT AND TRADEMARK OFFICE
CERTIFICATE OF CORRECTION

PATENT NO. : 4,710,634
DATED : December 1, 1987
INVENTOR(S) : Richard L. Brookes It is certified that error appears in the above-identified patent and that said Letters Patent is hereby corrected as shown below:

```
Title page, line 5 of the abstract, "proving" should
read -- providing --

Column 2, line 25, after "present", delete ",".
```

Signed and Sealed this

Seventh Day of June, 1988

*Attest:*

DONALD J. QUIGG

*Attesting Officer*     *Commissioner of Patents and Trademarks*